US010267678B2

(12) United States Patent
Zhao et al.

(10) Patent No.: US 10,267,678 B2
(45) Date of Patent: Apr. 23, 2019

(54) RAMAN SPECTROSCOPIC DETECTION METHOD

(71) Applicant: NUCTECH COMPANY LIMITED, Beijing (CN)

(72) Inventors: Ziran Zhao, Beijing (CN); Jianhong Zhang, Beijing (CN); Hongqiu Wang, Beijing (CN); Weiwei Wang, Beijing (CN); Zhiming Wang, Beijing (CN); Yumin Yi, Beijing (CN)

(73) Assignee: NUCTECH COMPANY LIMITED, Beijing (CN)

( * ) Notice: Subject to any disclaimer, the term of this patent is extended or adjusted under 35 U.S.C. 154(b) by 535 days.

(21) Appl. No.: 14/577,748

(22) Filed: Dec. 19, 2014

(65) Prior Publication Data
US 2015/0185076 A1    Jul. 2, 2015

(30) Foreign Application Priority Data

Dec. 27, 2013   (CN) .......................... 2013 1 0740981

(51) Int. Cl.
*G01N 21/00* (2006.01)
*G01J 3/00* (2006.01)
(Continued)

(52) U.S. Cl.
CPC .............. *G01J 3/0297* (2013.01); *G01J 3/28* (2013.01); *G01J 3/44* (2013.01); *G01N 21/65* (2013.01);
(Continued)

(58) Field of Classification Search
CPC .... G01J 3/0297; G01J 3/44; G01J 3/28; G01J 2003/4424; G01N 21/65; G01N 2201/12;
(Continued)

(56) References Cited

U.S. PATENT DOCUMENTS 4,619,528 A * 10/1986 Genack ..................... G01J 3/44
356/301
5,946,090 A * 8/1999 Tashiro ..................... G01J 3/10
356/301
(Continued)

FOREIGN PATENT DOCUMENTS

CN    101614667 A    12/2009
CN    102740762 A    10/2012
(Continued)

OTHER PUBLICATIONS

Lieber et al., "Automated Method for Subtraction of Fluorescence from Biological Raman Spectra", 2003, Applied Spectroscopy, vol. 57 No. 11 pp. 1363-1367 (Nov. 2003).*
(Continued)

*Primary Examiner* — Nikolay K Yushin
(74) *Attorney, Agent, or Firm* — Oliff PLC (57) ABSTRACT

Embodiments of the present invention provide a Raman spectroscopic inspection method, comprising the steps of: measuring a Raman spectrum of an object to be inspected successively to collect a plurality of Raman spectroscopic signals; superposing the plurality of Raman spectroscopic signals to form a superposition signal; filtering out a florescence interfering signal from the superposition signal; and identifying the object to be inspected on basis of the superposition signal from which the florescence interfering signal has been filtered out. By means of the above method, a desired Raman spectroscopic signal may be acquired by removing the interference caused by a florescence signal from a Raman spectroscopic inspection signal of the object. It may inspect correctly the characteristics of the Raman spectrum of the object so as to identify the object effectively.

7 Claims, 5 Drawing Sheets

(51) Int. Cl.
*G01J 3/02* (2006.01)
*G01J 3/44* (2006.01)
*G01N 21/65* (2006.01)
*G01J 3/28* (2006.01)

(52) U.S. Cl.
CPC ............... *G01J 2003/4424* (2013.01); *G01N 2201/06113* (2013.01); *G01N 2201/12* (2013.01)

(58) Field of Classification Search
CPC ......... G01N 21/01; G01N 2201/06113; G01N 21/651; G01N 21/12
See application file for complete search history.

(56) References Cited

U.S. PATENT DOCUMENTS

| | | | | |
|---|---|---|---|---|
| 6,205,354 B1* | 3/2001 | Gellermann | ............ | G01N 21/65 356/301 |
| 6,281,971 B1* | 8/2001 | Allen | ............ | G01J 3/02 356/301 |
| 7,092,852 B1* | 8/2006 | Kane | ............ | G01J 3/28 356/301 |
| 7,145,651 B2* | 12/2006 | Li | ............ | G01J 3/1256 356/301 |
| 7,177,022 B2* | 2/2007 | Wang | ............ | G01J 3/28 356/301 |
| 7,271,896 B2* | 9/2007 | Chan | ............ | G01N 33/54373 356/301 |
| 7,337,066 B2* | 2/2008 | Neiss | ............ | G01N 21/65 702/124 |
| 7,760,352 B2* | 7/2010 | Armstrong | ............ | G01N 21/65 356/301 |
| 7,899,650 B2* | 3/2011 | Yeshwantpur | ............ | G01N 21/65 356/301 |
| 8,547,550 B2* | 10/2013 | Carpenter | ............ | C12Q 1/02 356/300 |
| 8,570,507 B1* | 10/2013 | Cooper | ............ | G01J 3/44 356/301 |
| 2001/0034478 A1 | 10/2001 | Lambert et al. | | |
| 2004/0022684 A1 | 2/2004 | Heinze et al. | | |
| 2006/0275541 A1 | 12/2006 | Weimer | | |
| 2008/0100835 A1 | 5/2008 | Ban et al. | | |
| 2009/0237648 A1* | 9/2009 | Armstrong | ............ | G01N 21/65 356/72 |

FOREIGN PATENT DOCUMENTS

| | | |
|---|---|---|
| CN | 102759521 A | 10/2012 |
| WO | 02/01199 A1 | 1/2002 |

OTHER PUBLICATIONS

Dec. 20, 2016 Office Action issued in Chinese Patent Application No. 201310740981.9.
Aug. 18, 2017 Search Report issued in European Patent Application No. 14874921.1.

* cited by examiner

RAMAN SPECTROSCOPIC DETECTION METHOD

CROSS-REFERENCE TO RELATED APPLICATION

This application claims the benefit of Chinese Patent Application No. 201310740981.9 filed on Dec. 27, 2013 in the State Intellectual Property Office of China, the whole disclosure of which is incorporated herein by reference.

BACKGROUND OF THE INVENTION

Field of the Invention

The present disclosure relates to the technical field of Raman spectroscopic inspection, and in particular, to a method for identifying an object using Raman spectroscopy.

Description of the Related Art

Raman spectrum is a molecule vibration spectrum, which may reflect fingerprints of molecules and may be used for inspection of a matter. The Raman spectroscopy inspects and identifies a substance by detecting Raman spectra produced by Raman scattering effects of an exciting light by an object to be inspected. The Raman spectroscopy has been widely applied in fields such as liquid security inspection, jewel detection, explosive detection, drug detection, medicine detection and the like.

The Raman spectroscopy has a problem of interference of a florescence signal in matter inspection. The Raman scattering section of a molecule is significantly smaller than its florescence scattering section. Thus, when the florescence from a molecule of an object to be detected or the florescence from a package of an object to be detected is stronger, the Raman spectrum only occupies a tiny portion of a detected signal. When the Raman spectrum collected in test is relatively weak, it may typically be enhanced by increasing an exposure time. However, in order to protect a spectroscope, the intensity of Raman spectrum collected in each test will be limited to a threshold, and the spectrum will not be displayed in entirety if its intensity exceeds the threshold. Therefore, when the florescence interference is large, the collected Raman spectroscopic signal will be too weak to identify the matter.

At present, a main method of suppressing the florescence interference is to use a laser having a long wavelength and a weak florescence effect, such as 1064 nm laser, or to add a florescence Quencher, or to use a Raman enhance technology. The Raman spectroscopic signal collected by a long wavelength laser is often very weak and thus the detection time is long. In this way, it is very difficult to be used to detect the matter having low Raman effect. The florescence Quencher may introduce a strong Raman spectroscopic signal itself, which will adversely influence the accuracy of Raman spectrum data. The Raman enhance technology generally cannot eliminate the florescence interference from packages. In practice, the florescence interference from strong florescence matter or packages is very common. Thus, research for eliminating or reducing the adverse effects of florescence in Raman spectroscopy is very significant for expanding applications of the Raman spectroscopy.

SUMMARY OF THE INVENTION

An embodiment of the present invention provides a Raman spectroscopic inspection method, comprising the steps of:

(a) measuring a Raman spectrum of an object to be inspected successively to collect a plurality of Raman spectroscopic signals;
(b) superposing the plurality of Raman spectroscopic signals to form a superposition signal;
(c) filtering out a florescence interfering signal from the superposition signal; and
(d) identifying the object to be inspected on basis of the superposition signal from which the florescence interfering signal has been filtered out.

DETAILED DESCRIPTION OF PREFERRED EMBODIMENTS OF THE INVENTION

Exemplary embodiments of the present invention will be described hereinafter in detail with reference to the attached drawings, wherein the like reference numerals refer to the like elements. The present invention may, however, be embodied in many different forms and should not be construed as being limited to the embodiment set forth herein; rather, these embodiments are provided so that the present invention will be thorough and complete, and will fully convey the concept of the disclosure to those skilled in the art.

When a Raman spectroscopy is used to inspect an object, it may be interfered by a florescence. The florescence may be produced by the object to be inspection itself, or may be produced by other matters such as package matters or enhancing agents mixed in the object. The florescence spectrum may cover a frequency range of the Raman spectrum. Thus, in the Raman spectroscopic inspection, the Raman spectroscopic signal collected from the object may contain the florescence signal. When the florescence signal is strong, a characterizing peak may not be correctly extracted from the Raman spectroscopic signal to identify the object to be inspected. Therefore, removing such interference is very important for inspecting and identifying the object accurately and effectively.

Figure 1:
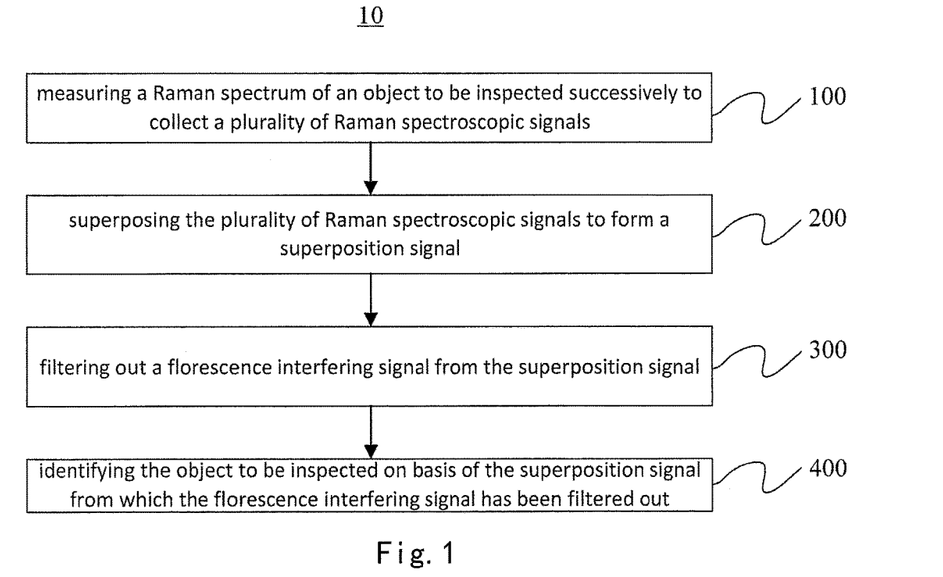
FIG. 1 shows a schematic flow chart of a Raman spectroscopic inspection method according to an embodiment of the present invention.

FIG. 1 shows a schematic flow chart of a Raman spectroscopic inspection method according to an embodiment of the present invention. The method 10 may include: step 100 of measuring a Raman spectrum of an object to be inspected successively to collect a plurality of Raman spectroscopic signals; step 200 of superposing the plurality of Raman spectroscopic signals to form a superposition signal; step 300 of filtering out a florescence interfering signal from the superposition signal; and step 400 of identifying the object to be inspected on basis of the superposition signal from which the florescence interfering signal has been filtered out.

In the prior art, signal intensity of the Raman spectrum may generally be enhanced by increasing the exposure time. However, in a practical Raman spectroscopic instrument, the Raman spectroscopic signal collected at a single time is limited to avoid adverse influence on the life of the instrument due to too large light power or too long work time. In the embodiment of the present invention, the Raman spectrum of the object to be inspected is successively measured and the collected plurality of Raman spectroscopic signals may be superposed to enhance the intensity of signal, thus, the above adverse influence may be avoided. The term of "plurality of" may for example represent two, three, four, five, ten, fifteen, fifty and the like.

Figure 2:
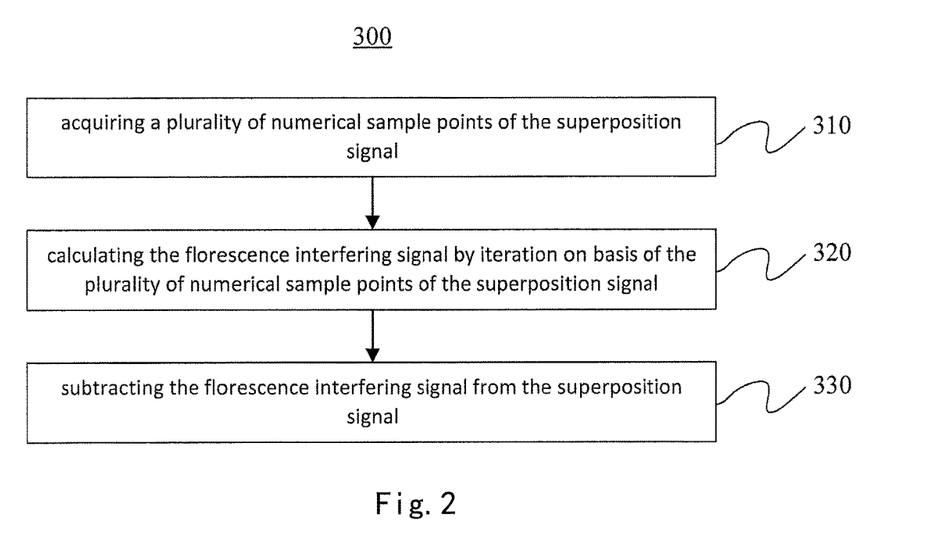
FIG. 2 shows a schematic flow chart of filtering out a florescence interference signal from a superposition signal according to an embodiment of the present invention.

As an example, as shown in FIG. 2, the step of filtering out a florescence interfering signal from the superposition signal may comprise the following steps: step 310 of acquiring a plurality of numerical sample points of the superposition signal, the number of the numerical sample points meeting the requirement of the sampling theorem; step 320 of calculating the florescence interfering signal by iteration on basis of the plurality of numerical sample points of the superposition signal; and step 330 of subtracting the florescence interfering signal from the superposition signal.

In order to calculate the florescence interference signal, the superposition signal needs to be in a discrete numerical form. If the superposition signal is a continuous simulation curve, then it needs to be converted into the discrete numerical form by a sampling process. However, in practice, the superposition signal is often in the discrete numerical form. In this case, it only needs to acquire numerical sample points directly. In order to ensure fidelity of the discrete signals, the number of the sample points should meet the requirement of the sampling theorem.

The florescence signal changes slowly and smoothly in comparison with the Raman characterizing signal. As an example, the florescence interference signal may be calculated by iteration as follow:

assuming that $\{y_n\}$ is a sequence of numerical sample points of the superposition signal, $y_n(i)$ is a value of the $i_{th}$ numerical sample point in $\{y_n\}$, and $\{y_{n+1}\}$ is the sequence which is calculated out after one iteration and $y_{n+1}(i)$ is a value of the $i_{t}$, numerical sample point in $\{y_{n+1}\}$, then $$y_{n+1}(i) = \min\left[y_n(i), \frac{y_n(i-m) + y_n(i+m)}{2}\right] \quad \text{equation (1)}$$

where m is a positive integer and has an initial value of 1, wherein the above iteration is performed repeatedly until m meets a predetermined threshold, where m is added by 1 per iteration. By the above iterative calculation, the florescence interference signal can be obtained.

In the above equation (1), "min[ . . . , . . . ]" represents an operation of selecting minimum. Obviously, the serial number of the numerical point in each iterative calculation should meet the condition that i−m>0 and i+m is not greater than the total length of the sequence $\{y_n\}$. If a numerical point does not meet the condition, it may maintain its original value constantly in the iterative calculation.

In an example, the predetermined threshold of m is determined depending on the smoothness of the superposition signal. For example, when two points spaced by 2×m in a sequence of iterative result have a width of wave number which is greater than a minimum peak width but smaller than a florescence envelope width, it may be determined that m meets the predetermined threshold.

In an example, in order to further improve the calculation accuracy, the superposition signal may be subject to a logarithm treatment or a square treatment before the above iterative calculation is performed.

Although in the above example, the calculation of the florescence interference signal is explained with reference to the iterative method as shown in equation (1), it should be understood that it is not necessary. The methods for solving a smooth spectrum signal in the art may also be used to solve the above florescence interference signal, but the method may be more complex and cause a low calculation efficiency.

Figure 3:
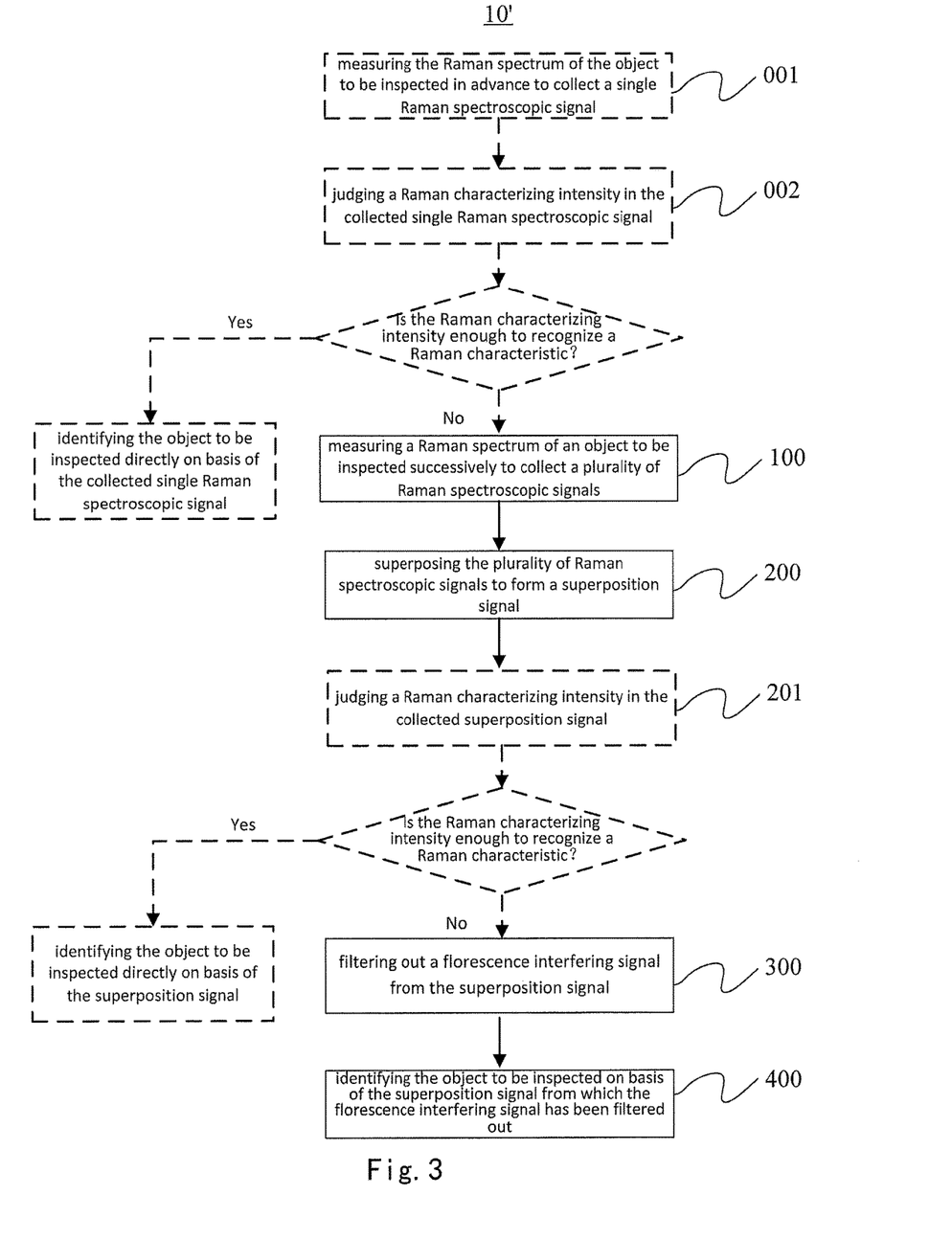
FIG. 3 shows a schematic flow chart of a Raman spectroscopic inspection method according to another embodiment of the present invention.

In another embodiment, the Raman spectroscopic inspection method 10' according to an embodiment of the present invention may further comprise an optional step, as indicated by the dashed part in FIG. 3. For example, the method may, before the step 100, further comprises: step 001 of measuring the Raman spectrum of the object to be inspected in advance to collect a single Raman spectroscopic signal; and step 002 of judging a Raman characterizing intensity in the collected single Raman spectroscopic signal. If the Raman characterizing intensity judged in the step 002 is enough to recognize a Raman characteristic, then identify the object to be inspected directly on basis of the collected single Raman spectroscopic signal without performing the subsequent steps; otherwise, if the Raman characterizing intensity is not enough to recognize the Raman characteristic, then continue to perform the step 100. It may improve the inspection efficiency by omitting the subsequent steps of performing successive measurements and filtering out the florescence interference in case that the florescence interference signal is weak for the object to be inspected and will not destroy the Raman spectroscopy.

As an example, in the step 001, the judgment of the Raman characterizing intensity may be done by searching a Raman characterizing peak in the single Raman spectroscopic signal; and if the Raman characterizing peak is found, then determining the Raman characterizing intensity is enough to recognize the Raman characteristic, otherwise, if the Raman characterizing peak is not found, then determining the Raman characterizing intensity is not enough to recognize the Raman characteristic.

As another example, in the step 001, the judgment of the Raman characterizing intensity may also be done by searching a Raman characterizing peak in the single Raman spectroscopic signal; and if the Raman characterizing peak is found and a ratio of an intensity of the Raman characterizing peak to an average intensity of the single Raman spectroscopic signal is greater than a predetermined first threshold, then determining the Raman characterizing intensity is enough to recognize the Raman characteristic, otherwise, if the Raman characterizing peak is not found, or the ratio of the intensity of the Raman characterizing peak to the average intensity of the single Raman spectroscopic signal is not greater than the predetermined first threshold although it is found, then determining the Raman characterizing intensity is not enough to recognize the Raman characteristic.

The above average intensity of the single Raman spectroscopic signal characterizes a combination of the characterizing intensity of the Raman spectrum and the intensity of the florescence interference signal. Thus, the ratio of the intensity of the Raman characterizing peak to the average intensity of the Raman spectroscopic signal reflects the contrast relation between the characterizing intensity of the Raman spectrum and the intensity of the florescence interference signal. The first threshold may be determined depending on instrument accuracy, calculation errors and the like, for example, it may be determined as 0.5, 1, 3 and the like.

The Raman spectroscopic inspection method, as shown in FIG. 3, between the step 200 and the step 300, may optionally further comprise: step 201 of judging a Raman characterizing intensity in the superposition signal. If the Raman characterizing intensity judged in the step 201 is enough to recognize a Raman characteristic, then identify the object to be inspected directly on basis of the superposition signal without performing the subsequent steps; otherwise, if the Raman characterizing intensity is not enough to recognize the Raman characteristic, then continue to perform the step 300. In the case that the Raman characterizing intensity and the intensity of the florescence interference signal are both weak, the Raman characteristic, for example the Raman characterizing peak, in the Raman spectroscopic signal may be detected correctly after enhancing the total intensity of the Raman spectroscopic signal by means of successive measurements and signal superposition. In this way, by means of the above step 201, calculation of the florescence interference signal may be avoided to improve the calculation efficiency.

As an example, in the step 201, the judgment of the Raman characterizing intensity may be done by searching a Raman characterizing peak in the superposition signal; and if the Raman characterizing peak is found, then determining the Raman characterizing intensity is enough to recognize the Raman characteristic, otherwise, if the Raman characterizing peak is not found, then determining the Raman characterizing intensity is not enough to recognize the Raman characteristic.

As another example, in the step 201, the judgment of the Raman characterizing intensity may also be done by searching a Raman characterizing peak in the superposition signal; and if the Raman characterizing peak is found and a ratio of an intensity of the Raman characterizing peak to an average intensity of the superposition signal is greater than a predetermined second threshold, then determining the Raman characterizing intensity is enough to recognize the Raman characteristic, otherwise, if the Raman characterizing peak is not found, or the ratio of the intensity of the Raman characterizing peak to the average intensity of the superposition signal is not greater than the predetermined second threshold although it is found, then determining the Raman characterizing intensity is not enough to recognize the Raman characteristic.

Similar to the above step 002, the above average intensity of the Raman spectroscopic signal characterizes a combination of the characterizing intensity of the Raman spectrum and the intensity of the florescence interference signal. Thus, the ratio of the intensity of the Raman characterizing peak to the average intensity of the Raman spectroscopic signal reflects the contrast relation between the characterizing intensity of the Raman spectrum and the intensity of the florescence interference signal. The second threshold may be determined depending on instrument accuracy, calculation errors and the like, for example, it may be determined as 0.5, 1, 3 and the like. The above second threshold may be same to the first threshold, or may be different from the first threshold.

In the above embodiments, the average intensity may be such as an arithmetical mean or a geometrical mean of the signal intensity.

Figure 4:
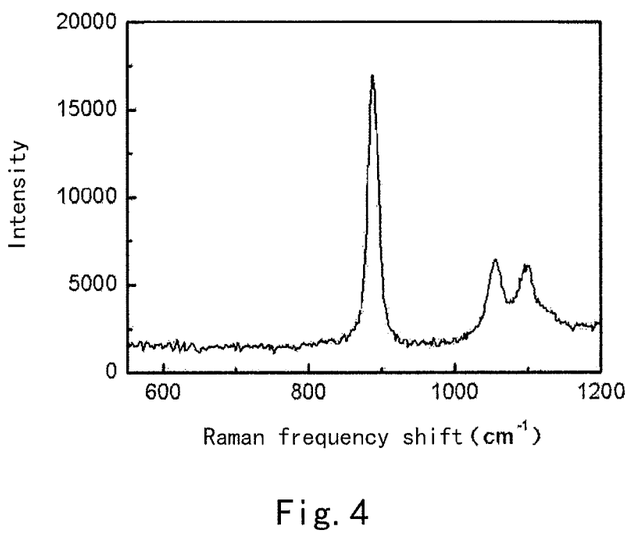
FIG. 4 shows schematically a single Raman spectroscopic signal of a first inspection example using a Raman spectroscopic inspection method according to an embodiment of the present invention.

FIG. 4 shows schematically a first example of an inspecting process using a Raman spectroscopic inspection method according to an embodiment of the present invention. In the example, the object to be inspected is anhydrous ethyl alcohol.

During inspection, a laser irradiates the anhydrous ethyl alcohol to acquire a Raman spectroscopic signal. The exposure time of the laser is one second, as illustrated in FIG. 4. As in the example, the florescence interference signal has a weak intensity in contrast to the characterizing peak in the Raman spectroscopic signal, the object to be inspected may be identified directly on basis of a single Raman spectroscopic signal. For example, it may be performed by using the above steps 001, 002. Of course, in this case, the above steps of performing successive measurements and filtering out the florescence interference signal can be performed without influencing the measurement results adversely.

Figure 5A:
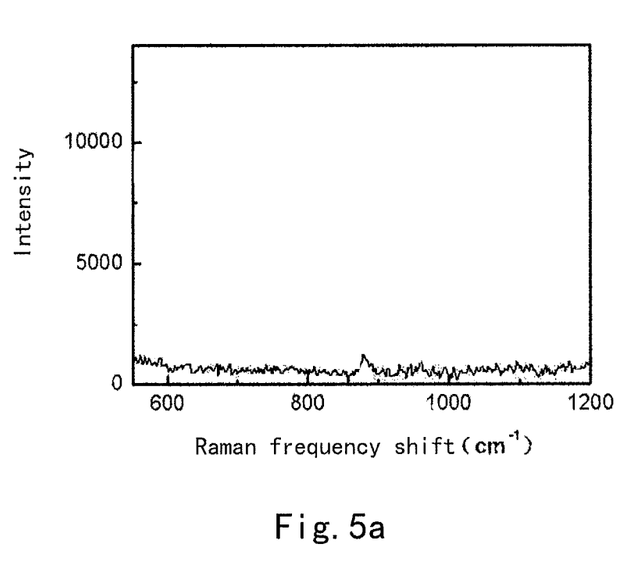
FIG. 5a-5b show schematically a single Raman spectroscopic signal and a superposition signal of a second inspection example using a Raman spectroscopic inspection method according to an embodiment of the present invention.
Figure 5B:
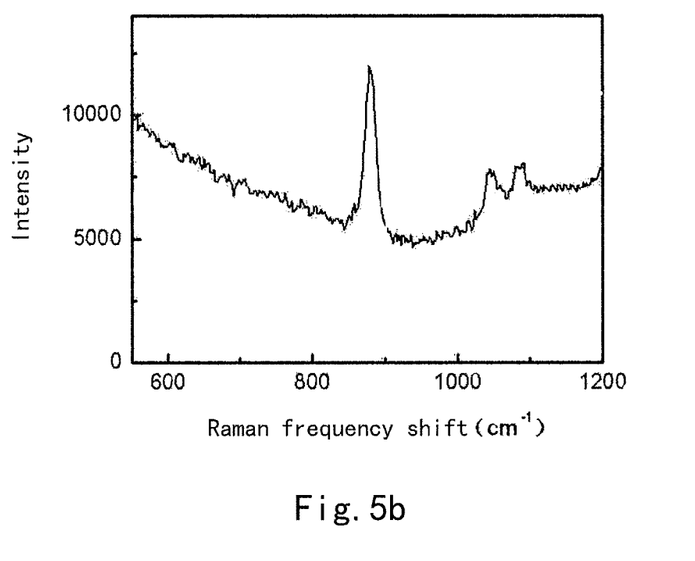

FIGS. 5a-5b show schematically a second example of a inspecting process using a Raman spectroscopic inspection method according to an embodiment of the present invention. In the example, the object to be inspected is a water solution with 5% alcohol.

During inspection, a laser irradiates the water solution with 5% alcohol to acquire a Raman spectroscopic signal, as illustrated in FIG. 5a. The exposure time of the laser is one second. As seen from FIG. 5a, the Raman spectroscopic signal has a weak intensity as a whole, and both the Raman characteristic and the florescence interference signal have weak intensities. In this case, the water solution with 5% alcohol is measured successively for twelve times and the detected Raman spectroscopic signals are superposed to obtain the superposition signal, as shown in FIG. 5b. In the circumstance shown in FIG. 5b, the Raman characterizing peaks at 879 $cm^{-1}$, 1046 $cm^{-1}$, 1084 $cm^{-1}$ can be detected already. Therefore, for this case, the object to be inspected may be identified directly on basis of the superposition signal without the subsequent steps 300 and 400, as shown in FIG. 3. Of Course, if the steps 300 and 400 are performed, the measurement results will not be influenced adversely, but will cause the loss of computation efficiency.

Figure 6A:
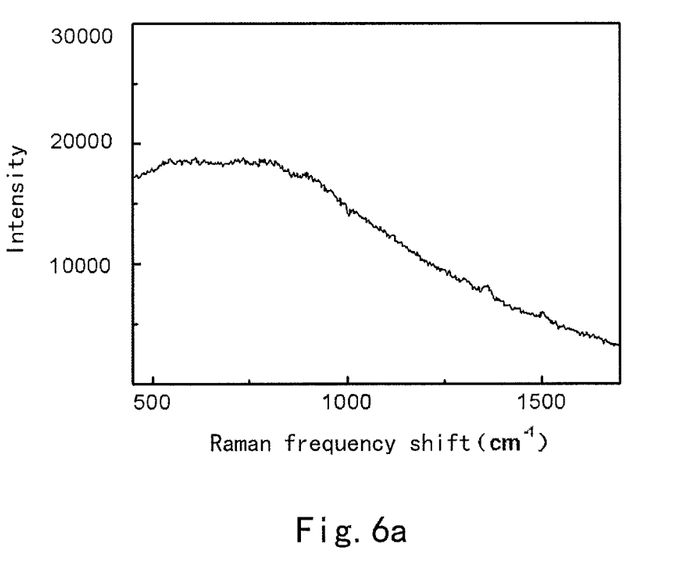
FIG. 6a-6c show schematically a single Raman spectroscopic signal, a superposition signal and the superposition signal, from which a florescence interference signal has been filtered out, of a third inspection example using a Raman spectroscopic inspection method according to an embodiment of the present invention.
Figure 6B:
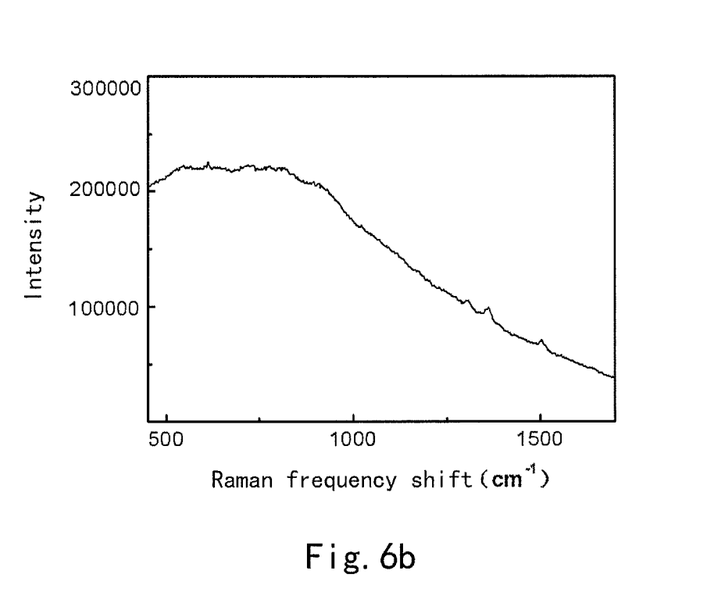
Figure 6C:
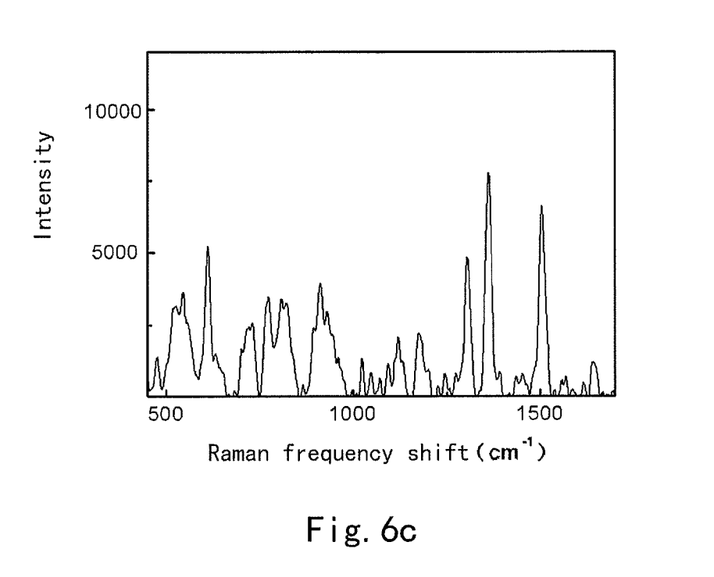

FIGS. 6a-6c show schematically a third example of a inspecting process using a Raman spectroscopic inspection method according to an embodiment of the present invention. In the example, the object to be inspected is rhodamine 6G disposed in a transparent glass bottle.

In the inspection, a single Raman spectroscopic signal is acquired by an exposure time of one second, as shown in FIG. 6a. As seen from FIG. 6a, no clear Raman characterizing peaks may be observed in the Raman spectroscopic signal. Ten Raman spectroscopic signals are obtained by successive measurements at ten times and superposed to acquire a result shown in FIG. 6b. From FIG. 6b, still no clear Raman characterizing peaks may be observed in the superposed Raman spectroscopic signal. Thus, the superposition signal cannot still be used to identify the object to be inspected. After the florescence signal is filtered out from the superposition signal, the resultant superposition signal is shown in FIG. 6c. In FIG. 6c, clear Raman characterizing peaks at 476 $cm^{-1}$, 610 $cm^{-1}$, 776 $cm^{-1}$, 914 $cm^{-1}$, 1122 $cm^{-1}$, 1176 $cm^{-1}$, 1304 $cm^{-1}$, 1360 $cm^{-1}$, 1504 $cm^{-1}$, 1642 $cm^{-1}$ may be observed. It can be determined accurately that the object to be inspected is rhodamine 6G by identifying the object using the signal as shown FIG. 6c.

By comparing FIGS. 6a-6c with one another, it can be seen that the characterizing peaks of the Raman spectroscopic signal of the object to be inspected are almost masked when the florescence interference signal is very strong. However, the characterizing peaks of the Raman spectroscopic signal of the object may be correctly found by the Raman spectroscopic inspection method according to embodiments of the present invention such that the object to be inspected may be identified correctly and efficiently.

Although the present invention has been explained with reference to the drawings, the embodiments shown in the drawings are only illustrative, instead of limiting the present invention.

Although some embodiments of the general inventive concept are illustrated and explained, it would be appreciated by those skilled in the art that modifications and variations may be made in these embodiments without departing from the principles and spirit of the general inventive concept of the disclosure, the scope of which is defined in the appended claims and their equivalents.

What is claimed is:

1. A Raman spectroscopic inspection method, comprising the steps of:
   (a-1) irradiating an object to be inspected by a laser at a fixed wavelength, such that a spectrum is generated from the irradiated object under a Raman scattering effect;
   (a) performing a plurality of successive measurements of the spectrum generated from the object to collect a plurality of spectroscopic signals comprising Raman and florescence signals of the object respectively by a Raman spectroscopic instrument;
   (b) adding up the plurality of spectroscopic signals comprising Raman and florescence signals to form a superposition signal, for enhancing the intensity of signal;
   (c) filtering out the florescence signal from the superposition signal; and
   (d) identifying the object to be inspected on basis of the superposition signal from which the florescence signal has been filtered out,
   wherein the step (c) comprises:
   (c1) acquiring a plurality of numerical sample points of the superposition signal, a number of the numerical sample points meeting a requirement of a sampling theorem;
   (c2) calculating the florescence signal by iteration on basis of the plurality of numerical sample points of the superposition signal; and
   (c3) subtracting the florescence signal from the superposition signal, and
   wherein in the step (c2), the florescence signal is calculated by iteration as follow:
   assuming that $\{y_n\}$ is a sequence of numerical sample points of the superposition signal, $y_n(i)$ is a value of the $i_{th}$ numerical sample point in $\{y_n\}$, and $\{y_{n+1}\}$ is a sequence which is calculated out after one iteration and $y_{n+1}(i)$ is a value of the $i_{th}$ numerical sample point in $\{y_{n+1}\}$, then $$y_{n+1}(i) = \min\left[y_n(i), \frac{y_n(i-m) + y_n(i+m)}{2}\right]$$

where m is a positive integer and has an initial value of 1, wherein the above iteration is performed repeatedly until m meets a predetermined threshold, where m is added by 1 per iteration.

2. The Raman spectroscopic inspection method according to claim 1, wherein the method, before the step (a), further comprises:
   (a00) measuring the spectrum of the object to be inspected in advance to collect a single spectroscopic signal; and
   (a01) judging a Raman characterizing intensity in the collected single spectroscopic signal, and if the Raman characterizing intensity is enough to recognize a Raman characteristic, then identifying the object to be inspected directly on basis of the collected single spectroscopic signal without performing the subsequent steps, otherwise, if the Raman characterizing intensity is not enough to recognize the Raman characteristic, then continuing to perform the step (a).

3. The Raman spectroscopic inspection method according to claim 2, wherein in the step (a01), the judgment of the Raman characterizing intensity is done by searching a Raman characterizing peak in the single spectroscopic signal; and if the Raman characterizing peak is found, then determining the Raman characterizing intensity is enough to recognize the Raman characteristic, otherwise, if the Raman characterizing peak is not found, then determining the Raman characterizing intensity is not enough to recognize the Raman characteristic.

4. The Raman spectroscopic inspection method according to claim 2, wherein in the step (a01), the judgment of the Raman characterizing intensity is done by searching a Raman characterizing peak in the single spectroscopic signal; and if the Raman characterizing peak is found and a ratio of an intensity of the Raman characterizing peak to an average intensity of the single spectroscopic signal is greater than a predetermined first threshold, then determining the Raman characterizing intensity is enough to recognize the Raman characteristic, otherwise, if the Raman characterizing peak is not found, or the ratio of the intensity of the Raman characterizing peak to the average intensity of the single spectroscopic signal is not greater than the predetermined first threshold although it is found, then determining the Raman characterizing intensity is not enough to recognize the Raman characteristic.

5. The Raman spectroscopic inspection method according to claim 1, wherein the method, between the step (b) and the step (c), further comprises:
   (b1) judging a Raman characterizing intensity in the superposition signal, and if the Raman characterizing intensity is enough to recognize a Raman characteristic, then identifying the object to be inspected directly on basis of the superposition signal without performing the subsequent steps, otherwise, if the Raman characterizing intensity is not enough to recognize the Raman characteristic, then continuing to perform the step (a).

6. The Raman spectroscopic inspection method according to claim 5, wherein in the step (b1), the judgment of the Raman characterizing intensity is done by searching a Raman characterizing peak in the superposition signal; and if the Raman characterizing peak is found, then determining the Raman characterizing intensity is enough to recognize the Raman characteristic, otherwise, if the Raman characterizing peak is not found, then determining the Raman characterizing intensity is not enough to recognize the Raman characteristic.

7. The Raman spectroscopic inspection method according to claim 5, wherein in the step (b1), the judgment of the Raman characterizing intensity is done by searching a Raman characterizing peak in the superposition signal; and if the Raman characterizing peak is found and a ratio of an intensity of the Raman characterizing peak to an average intensity of the superposition signal is greater than a predetermined second threshold, then determining the Raman characterizing intensity is enough to recognize the Raman characteristic, otherwise, if the Raman characterizing peak is not found, or the ratio of the intensity of the Raman characterizing peak to the average intensity of the superposition signal is not greater than the predetermined second threshold although it is found, then determining the Raman characterizing intensity is not enough to recognize the Raman characteristic.

\* \* \* \* \*